(12) United States Patent
Ando

(10) Patent No.: US 6,623,617 B2
(45) Date of Patent: Sep. 23, 2003

(54) METHOD AND APPARATUS FOR MEASURING CONCENTRATION OF A COMPONENT IN A GAS

(75) Inventor: Masashi Ando, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 54 days.

(21) Appl. No.: 09/370,924

(22) Filed: Aug. 10, 1999

(65) Prior Publication Data

US 2003/0010653 A1 Jan. 16, 2003

(30) Foreign Application Priority Data

Aug. 10, 1998 (JP) .......................... 10-225863

(51) Int. Cl.$^7$ ............................ G01N 27/407
(52) U.S. Cl. ................... 205/781; 205/783.5; 204/425; 204/426
(58) Field of Search .............. 205/781, 783.5, 205/784, 785; 204/425, 426; 123/693, 694, 695

(56) References Cited

U.S. PATENT DOCUMENTS

| | | | |
|---|---|---|---|
| 5,285,676 A | * | 2/1994 | Adams ..................... 73/23.32 |
| 5,672,811 A | | 9/1997 | Kato et al. ................. 204/425 |
| 5,780,710 A | | 7/1998 | Murase et al. |
| 5,866,799 A | | 2/1999 | Kato et al. |
| 5,939,615 A | | 8/1999 | Kato et al. |

FOREIGN PATENT DOCUMENTS

| | | |
|---|---|---|
| EP | 0 678 740 A1 | 10/1995 |
| EP | 0 791 828 A1 | 8/1997 |
| EP | 0 798 555 A2 | 10/1997 |
| EP | 0 807 818 A2 | 11/1997 |
| EP | 0 841 562 A2 | 5/1998 |
| EP | 0 859 232 A2 | 8/1998 |
| EP | 0 878 709 A2 | 8/1998 |
| EP | 0 863 399 A2 | 9/1998 |
| GB | 2 288 873 A | 11/1995 |
| JP | 9-264861 | 10/1997 |
| JP | 10--90220 | 4/1998 |
| JP | 11-23528 | 1/1999 |
| JP | 11-108887 | 4/1999 |

OTHER PUBLICATIONS

Harris, "Quantitative Chemical Analysis", 4th edition, pp. 137–140.*
Strobel et al., "Chemical Instrumentation: A Systematic Approach", 3rd edition, pp. 385–389.*
Skoog, "Principles of Instrumental Analysis", 3rd edition, pp. 628–630.*
European Search Report for Application No. EP 99 30 6296.

* cited by examiner

Primary Examiner—Nam Nguyen
Assistant Examiner—Kaj K. Olsen
(74) Attorney, Agent, or Firm—Sughrue Mion, PLLC

(57) ABSTRACT

A method and apparatus which enable accurate measurement of the concentration of NOx in a gas under measurement, even when the NOx concentration is low. A gas under measurement is introduced into a first chamber 3 through a first diffusion passage 2. A pump voltage V1 is applied from a direct-current power source E1 to a first oxygen ion pump cell 6 such that the electric potential of an oxygen-concentration-measuring cell 7 is held constant. As a result, oxygen is pumped out from the first chamber 3 such that the oxygen concentration measured at an inlet to a second chamber 5 becomes constant. A first pump current $I_{p1}$ flowing to the first oxygen ion pump cell 6 is measured. Next, the gas under measurement contained in the first chamber 3 is introduced into the second chamber 5 through a second diffusion passage 4. A pump voltage V2 is applied to a second oxygen ion pump cell 8 of the second chamber 5 by means of a direct-current power source E2, thereby decomposing nitrogen monoxide contained in the gas under measurement and pumping out oxygen from the second chamber 5. A second pump current $I_{p2}$ flowing to the second oxygen ion pump cell 8 is measured. In a measurement region in which NOx concentration is low, the second pump current $I_{p2}$ is proportional to the square of the NOx concentration. Thus, the NOx concentration is obtained from the second pump current $I_{p2}$ by use of an expression of second order.

16 Claims, 2 Drawing Sheets

METHOD AND APPARATUS FOR MEASURING CONCENTRATION OF A COMPONENT IN A GAS

BACKGROUND OF THE INVENTION

1. Field of the Invention

The present invention relates to a method and apparatus for measuring the concentration of a component of a gas to be measured (hereinafter referred to as a "gas under measurement"). In particular, the invention relates to measuring the concentration of nitrogen oxides (hereinafter referred to as "NOx") in a gas under measurement. More particularly, the invention relates to a method for measuring the concentration of NOx in exhaust gas from, for example, a combustor or an internal combustion engine.

2. Description of the Prior Art

Conventionally, a method for measuring the concentration of NOx in a gas under measurement employs an NOx concentration sensor including a first chamber and a second chamber, each including an oxygen ion pump cell.

According to the conventional method, first, a gas under measurement (for example, exhaust gas from a combustor or an internal combustion engine) is introduced into the first chamber through a first diffusion passage (for example, a diffusion controlling hole). A pump voltage is applied to a first oxygen ion pump cell of the first chamber in order to pump out oxygen from the first chamber such that oxygen concentration measured at an inlet to the second chamber becomes constant and such that the voltage of an oxygen-concentration-measuring cell becomes constant. At this time, not only is oxygen contained in the introduced gas decomposed, but also nitrogen monoxide contained in the gas is decomposed to a certain extent. The first pump current $I_{p1}$ flowing to the first oxygen ion pump cell is measured. The first pump current $I_{p1}$ is proportional to the amount of oxygen ions generated through decomposition of oxygen and nitrogen monoxide contained in the gas introduced into the first chamber.

Next, the gas under measurement contained in the first chamber is introduced into the second chamber through a second diffusion passage (for example, a diffusion controlling hole). A pump voltage is applied to a second oxygen ion pump cell of the second chamber so as to decompose nitrogen monoxide contained in the introduced gas and to pump out oxygen from the second chamber. The second pump current $I_{p2}$ flowing through the second oxygen ion pump is measured.

FIG. 3 shows the relationship between the concentration of NOx in the gas under measurement introduced into the first chamber and the second pump current $I_{p2}$. From the relationship shown in FIG. 3, the concentration of NOx is obtained by expression (1).

$$\text{NOx concentration} = G(I_2 - \beta) \quad (1)$$

where $\beta$: Offset component of second pump current $I_{p2}$

G: Gain ppm/A

The offset component $\beta$ is the value of the second pump current $I_{p2}$ as measured at an NOx concentration of 0 ppm and corresponds to a pump current which is generated in relation to decomposition of residual oxygen which has not been decomposed in the first chamber and remains in the gas introduced into the second chamber.

Measurement of the offset component $\beta$ employs a standard gas having an NOx concentration of 0 ppm and a known oxygen concentration. The offset component $\beta$ is measured through measurement of the second pump current $I_{p2}$ while the concentration of oxygen in the standard gas is varied. Measurement of the gain G employs a standard gas having a constant oxygen concentration and a known NOx concentration. The gain G is measured through measurement of the second pump current $I_{p2}$ while the concentration of NOx in the standard gas is varied. The gain G and the offset component $\beta$ depend on the concentration of oxygen in the gas under measurement, whereas the concentration of oxygen in the gas under measurement is measured substantially accurately through measurement of the first pump current $I_{p1}$. Accordingly, the gain G must be corrected on the basis of the first pump current $I_{p1}$.

However, according to the above-described method, the NOx concentration can be measured accurately in a measurement region in which the second pump current $I_{p2}$ has a high value (a measurement region in which NOx concentration is high), whereas the NOx concentration cannot be measured accurately in a measurement region in which the second pump current $I_{p2}$ has a low value.

It is confirmed that the first pump current $I_{p1}$ is proportional to the concentration of oxygen in the gas under measurement. However, the reason why the above-mentioned expression (1) does not hold in the measurement region in which NOx concentration is low cannot be satisfactorily explained from a physical phenomenon associated with diffusion.

SUMMARY OF THE INVENTION

An object of the present invention is to solve the above-mentioned problems, and to provide a method for accurately measuring the concentration of NOx in a gas under measurement even in a measurement region in which NOx concentration is low.

To achieve the above object, the present invention provides a method for measuring the concentration of NOx in a gas under measurement by use of an NOx concentration sensor comprising: a first chamber equipped with a first oxygen ion pump cell, which comprises a solid electrolyte layer and a pair of electrodes; a second chamber equipped with a second oxygen ion pump cell, which comprises a solid electrolyte layer and a pair of electrodes; a first diffusion passage for establishing communication between the first chamber and the gas under measurement; and a second diffusion passage for establishing communication between the first chamber and the second chamber. The method comprises the steps of: applying a pump voltage to the first oxygen ion pump cell so as to reduce the concentration of oxygen in the gas under measurement to be introduced into the second chamber to such an extent that nitrogen monoxide is decomposed within the first chamber, as well as to pump out oxygen generated through decomposition of nitrogen monoxide, or pump oxygen into the first chamber; applying a pump voltage to the second oxygen ion pump cell in order to decompose nitrogen monoxide contained in the gas under measurement introduced into the second chamber; measuring a first pump current flowing through the first oxygen ion pump cell; measuring a second pump current flowing through the second oxygen ion pump cell; and obtaining from the second pump current the concentration of NOx in the gas under measurement introduced into the first chamber by use of a nonlinear expression which expresses an approximated relationship between the second pump current and the concentration of NOx in the gas under measurement.

Since, according to the present invention, the NOx concentration is determined by use of a nonlinear expression which expresses an approximated relationship between the second pump current and the concentration of NOx in the gas under measurement, the NOx concentration can be determined more accurately even in a measurement region in which NOx concentration is low, as compared to the conventional method that employs a linear expression.

Preferably, in the method for measuring the concentration of NOx in a gas under measurement, the concentration of oxygen in the gas under measurement introduced into the first chamber may be obtained from the first pump current by use of a nonlinear expression which expresses an approximated relationship between the first pump current and the concentration of oxygen in the gas under measurement.

Preferably, in the method for measuring the concentration of NOx in a gas under measurement, a coefficient of the nonlinear expression may be obtained from the first pump current.

Preferably, in the method for measuring the concentration of NOx in a gas under measurement, a provisional NOx concentration may be obtained from the second pump current by use of a linear expression which approximates the NOx concentration in terms of the second pump current, and the thus obtained provisional NOx concentration may be corrected by use of an expression of higher order to thereby obtain the concentration of NOx in the gas under measurement introduced into the first chamber. Notably, a coefficient of the expression of higher order is obtained from the relationship between the provisional NOx concentration and an actual NOx concentration.

Preferably, in the method for measuring the concentration of NOx in a gas under measurement, a provisional NOx concentration may be obtained from the second pump current by use of a linear expression which approximates the NOx concentration in terms of the second pump current, and a deviation of the provisional NOx concentration from an actual NOx concentration as approximated by an expression of higher order may be added to the provisional NOx concentration to thereby obtain the concentration of NOx in the gas under measurement introduced into the first chamber.

Embodiments of the invention will now be described, by way of example only, with reference to the accompanying drawings.

DESCRIPTION OF SYMBOLS USED IN THE DRAWINGS

Figure 1:
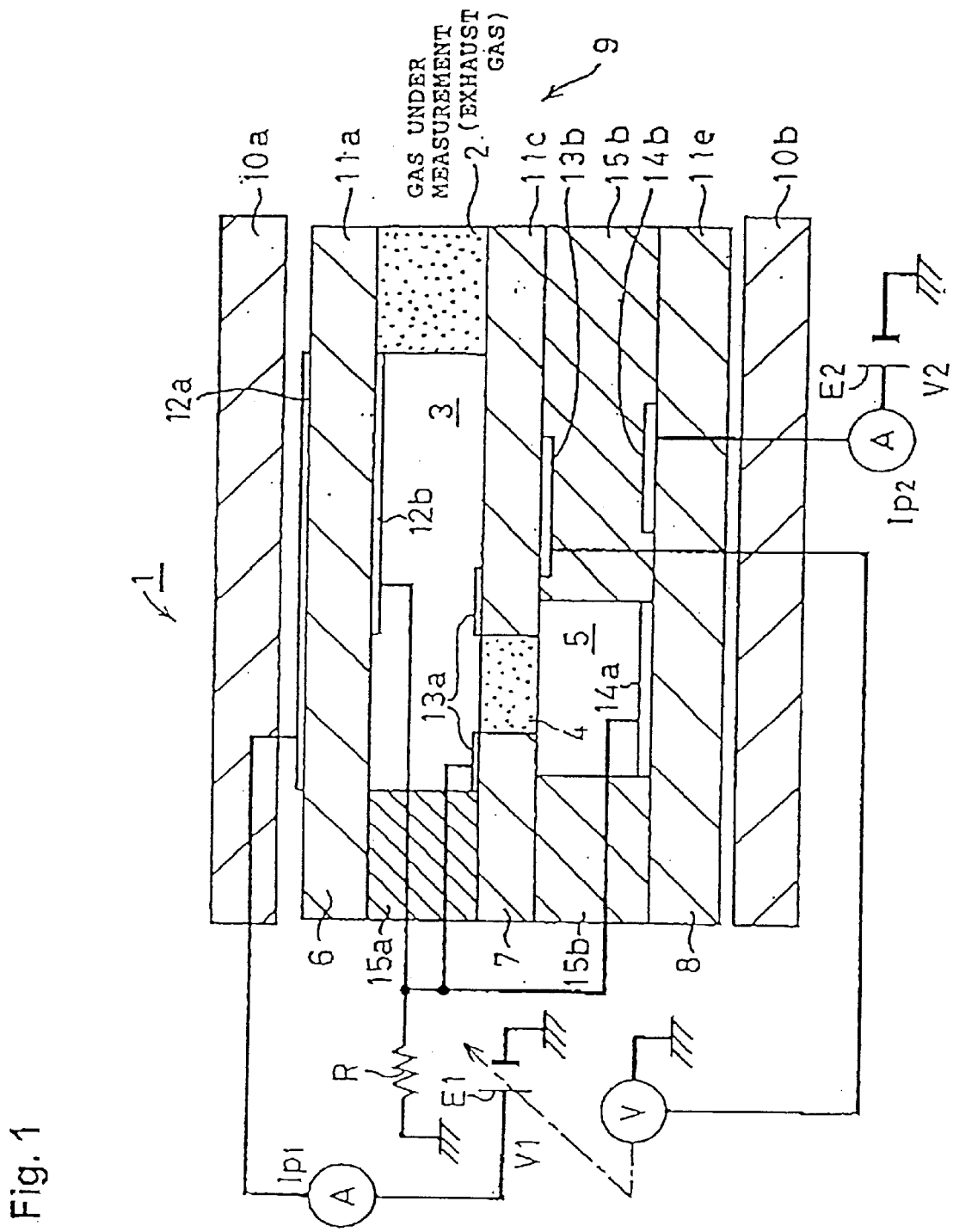
FIG. 1 is a sectional view showing a main portion of an NOx concentration sensor employed in first through third embodiments of the present invention.

1: NOx concentration sensor
2: first diffusion passage
3: first chamber
4: second diffusion passage
5: second chamber
6: first oxygen ion pump cell
8: second oxygen ion pump cell
11a–11e: solid electrolyte layers
12a, 12b, 13a, 13b, 14a, 14b: porous electrodes V1, V2: pump voltages
$I_{p1}$: first pump current
$I_{p2}$: second pump current

DESCRIPTION OF THE PREFERRED EMBODIMENTS (First Embodiment)

A first embodiment of the present invention will next be described with reference to the drawings.

FIG. 1 is a sectional view showing a main portion of an NOx concentration sensor 1 employed in the first embodiment.

The NOx concentration sensor 1 includes a sensor body 9 and heaters 10a and 10b. The sensor body 9 includes a first diffusion passage 2, a first chamber 3, a second diffusion passage 4, a second chamber 5, a first oxygen ion pump cell 6, an oxygen-concentration-measuring cell 7, and a second oxygen ion pump cell 8.

The sensor body 9 is composed of thin solid electrolyte layers 11a, 11c, and 11e of zirconia arranged in layers of this order. In order to electrically insulate the solid electrolyte layers 11a, 11c, and 11e from one another, an insulating layer 15a of alumina is interposed between the solid electrolyte layers 11a and 11c, and an insulating layer 15b of alumina is interposed between the solid electrolyte layers 11c and 11e.

The first oxygen ion pump cell 6 includes the solid electrolyte layer 11a and a pair of porous electrodes 12a and 12b disposed on opposite sides of the solid electrolyte layer 11a. The oxygen-concentration-measuring cell 7 includes the solid electrolyte layer 11c and a pair of porous electrodes 13a and 13b disposed on opposite sides of the solid electrolyte layer 11c. The second oxygen ion pump cell 8 includes the solid electrolyte layer 11e and a pair of porous electrodes 14a and 14b disposed on the same side of the solid electrolyte layer 11e.

The first chamber 3 is enclosed by the solid electrolyte layers 11a and 11c and the insulating layer 15a and is equipped with the first oxygen ion pump cell 6 and the oxygen-concentration-measuring cell 7. The porous electrodes 12b and 13a are disposed within the first chamber 3. The first chamber 3 communicates with a gas under measurement (for example, exhaust gas from a combustor or an internal combustion engine) through the first diffusion passage 2 interposed between the solid electrolyte layers 11a and 11c. The second chamber 5 is enclosed by the solid electrolyte layers 11c and 11e and the insulating layer 15b and is equipped with the second oxygen ion pump cell 8. The porous electrode 14a is disposed within the second chamber 5. The second chamber 5 communicates with the first chamber 3 through the second diffusion passage 4 extending through the solid electrolyte layer 11c.

The diffusion passages 2 and 4 control diffusion and assume the form of, for example, a fired body of alumina powder that has a diffusion hole formed therein in order to control diffusion.

The solid electrolyte layers 11a, 11c, and 11e are each formed from, for example, $ZrO_2$ green sheet.

The insulating layers 15a and 15b are each formed from, for example, $Al_2O_3$ paste or $Al_2O_3$ green sheet.

The flat heaters 10a and 10b face the solid electrolyte layers 11a and 11e, respectively, so that the sensor body 9 is sandwiched between the heaters 10a and 10b. The temperature of the sensor body 9 is controlled to 550° C. to 900° C. by use of the heaters 10a and 10b. Since the decomposition rate of NOx varies with temperature, the temperature of the sensor body 9 is controlled so as to measure the NOx concentration within a temperature range within which the decomposition rate does not vary. The heater 10b may be omitted.

The porous electrodes 12b, 13a, and 14a are grounded by way of a resistor R. The positive pump voltage V1 is applied from a direct-current power source E1 to the porous electrode 12a, and the first pump current $I_{p1}$ flowing from the direct-current power source E1 to the porous electrode 12a is measured. The positive pump voltage V2 is applied from a direct-current power source E2 to the porous electrode 14b, and the second pump current $I_{p2}$ flowing from the direct-current power source E2 to the porous electrode 14a is measured.

Next will be described a method for measuring the concentration of NOx in a gas under measurement by use of the above-described NOx concentration sensor 1.

First, the gas under measurement is introduced into the first chamber 3 through the first diffusion passage 2. The pump voltage V1 is then applied to the first oxygen ion pump cell 6 of the first chamber 3 by means of the direct-current power source E1 such that the electric potential of the oxygen-concentration-measuring cell 7 is held constant. As a result, oxygen is pumped out from the first chamber 3 such that the oxygen concentration measured at an inlet to the second chamber 5 becomes constant. At this time, not only is oxygen contained in the gas under measurement decomposed, but also nitrogen monoxide is decomposed to a certain extent. The first pump current $I_{p1}$ flowing to the first oxygen ion pump cell 6 is measured. The first pump current $I_{p1}$ is proportional to the amount of oxygen ions generated through decomposition of oxygen and nitrogen monoxide contained in the gas under measurement.

Next, the gas under measurement contained in the first chamber 3 is introduced into the second chamber 5 through the second diffusion passage 4. The pump voltage V2 is applied to the second oxygen ion pump cell 8 of the second chamber 5 by means of the direct-current power source E2, thereby decomposing nitrogen monoxide contained in the gas under measurement and pumping out oxygen from the second chamber 5. The second pump current $I_{p2}$ flowing to the second oxygen ion pump cell 8 is measured.

Notably, when the gas under measurement is introduced into the first chamber 3, the pump voltage V1 is controlled such that the electric potential of the oxygen-concentration-measuring cell 7 becomes constant, in order to render the oxygen concentration measured at the inlet to the second chamber 5 constant, thereby highly accurately controlling the concentration of oxygen in the gas under measurement introduced from the first chamber 3 into the second chamber 5.

Figure 2:
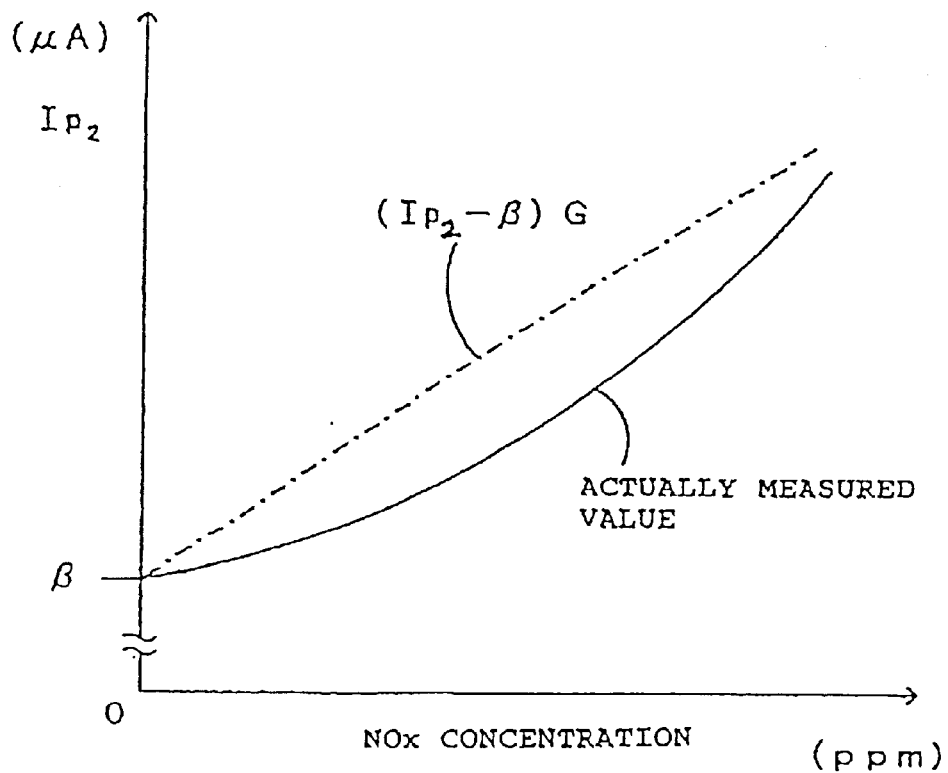
FIG. 2 is a graph showing an actual relationship between the second pump current $I_{p2}$ and the NOx concentration.

FIG. 2 shows the results of an experiment in measuring the NOx concentration in a measurement region in which the second pump current $I_{p2}$ has a low value (a measurement region in which NOx concentration is low), by the above-described method in which a standard gas of a known NOx concentration is employed as a gas under measurement.

Figure 3:
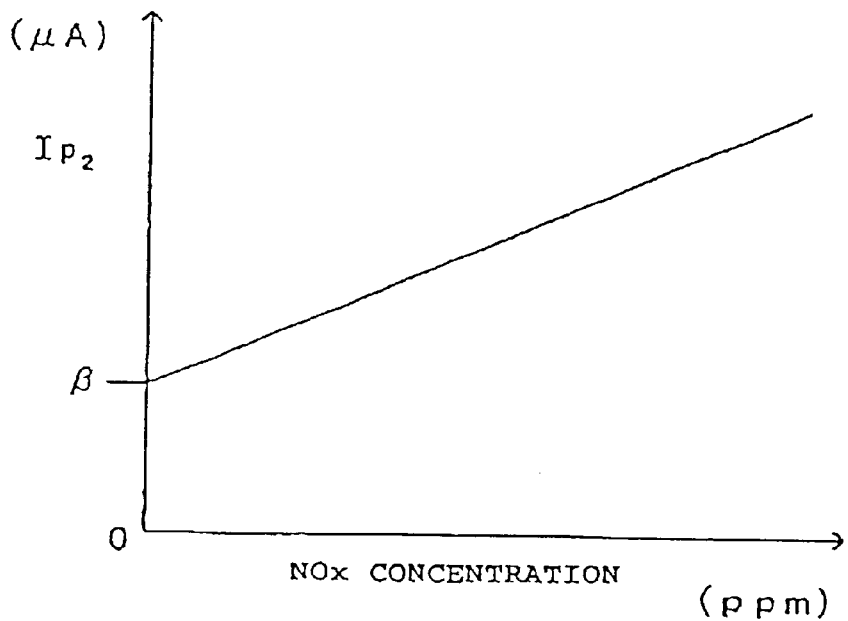
FIG. 3 is a graph showing a conventionally accepted relationship between the second pump current $I_{p2}$ and the NOx concentration.

FIG. 3 and the aforementioned expression (1) assume that the second pump current $I_{p2}$ is proportional to the NOx concentration. However, the results of the experiment have revealed that, in a measurement region in which the second pump current $I_{p2}$ has a low value, a measured value of the NOx concentration becomes smaller than a value of the NOx concentration calculated by expression (1); specifically, the second pump current $I_{p2}$ is proportional to the square of the concentration of NOx in a gas under measurement.

Accordingly, the NOx concentration can be obtained by expression (2).

$$NOx \text{ concentration} = \frac{b + \sqrt{b^2 + 4aG(I_{p2} - \beta)}}{2a} \quad (2)$$

where $\beta$: Offset component of second pump current $I_{p2}$ a: Coefficient, b: constant In order to obtain the constants a and b and the offset component $\beta$, the second pump current $I_{p2}$ may be measured by use of standard gases of known values of NOx concentration and oxygen concentration. The constants a and b and the offset component $\beta$ depend on the concentration of oxygen in the gas under measurement, whereas the concentration of oxygen in the gas under measurement is measured substantially accurately through measurement of the first pump current $I_{p1}$. Accordingly, the offset component $\beta$ can be calculated from the first pump current $I_{p1}$. Also, since the constants a and b depend on the NOx concentration, the constants a and b can be obtained on the basis of the known NOx concentration and oxygen concentration.

As described above, since the method of the first embodiment utilizes the phenomenon that, in a measurement region in which the second pump current $I_{p2}$ has a low value, the second pump current $I_{p2}$ is proportional to the square of the concentration of NOx in the gas under measurement, the method can accurately measure the NOx concentration even in a measurement region in which NOx concentration is low.

Notably, the phenomenon that the second pump current $I_{p2}$ is proportional to the square of the NOx concentration can be analyzed as represented by the following expressions (3) to (7).

In the following expressions,

| | | |
|---|---|---|
| R: | Gas constant | [J/mol · K] |
| T: | Absolute temperature | [K] |
| F: | Faraday's constant | [C/mol] |
| e: | Elementary charge | [c] |
| $P_{os3}$: | Partial pressure of oxygen within second chamber 5 | [Pa] |
| $P_{or2}$: | Partial pressure of oxygen within virtual space in which porous electrode 14b is supposed to be disposed | [Pa] |
| $R_{ip2}$: | Internal resistance of second oxygen ion pump cell 8 | [Ω] |
| k: | Boltzmann constant | [J/K] |
| $l_1$: | Length of first diffusion passage 2 | [m] |
| $l_3$: | Length of second diffusion passage 5 | [m] |
| $A_1$: | Sectional area of first diffusion passage 2 | [m²] |
| $A_3$: | Sectional area of second diffusion passage 5 | [m²] |
| $D_1, D_3$: | Diffusion constants | [m²/sec] |
| $P_{Oe(NO)}$: | Partial pressure of oxygen generated through decomposition of NOx within second chamber 5 | [Pa] |
| $K_{NO}$: | Pressure equilibrium constant | [-] |
| $P_{N2}$: | Partial pressure of nitrogen in gas under measurement | [Pa] |
| $P_{NOe}$: | Partial pressure of NOx in gas under measurement | [Pa] |

$$\frac{I_{p2}}{4e} = \frac{D_1 A_1}{KTl_1} P_{Oe(NO)} \bigg/ \left(1 + \frac{D_1 A_1 l_3}{D_3 A_3 l_1} \frac{1}{10^{(V_{p2}/0.05)} - K_3}\right) \quad (3)$$

$$V_{p2} = \frac{RT}{4F} \ln\left(\frac{P_{or2}}{P_{os3}}\right) + I_{p2} R_{ip2} \approx 0.05 T \log\left(\frac{P_{or2}}{P_{os3}}\right) + I_{p2} R_{ip2} \quad (4)$$

-continued $$K3 = P_{os2}/P_{os3} \quad (5)$$

$$K3 = P_{os2}/P_{os3} \quad (5)$$

Decomposition of NOx is represented by chemical equilibrium of expression (6).

$$2NO \rightleftharpoons N_2 + O_2$$

$$K_{NO} = \frac{P_{N2}P_{Oe(NO)}}{P_{NOe}^2} \quad (6)$$

$$\therefore P_{Oe(NO)} = K_{NO}\frac{P_{NOe}^2}{P_{N2}}$$

Expressions (3) and (6) give expression (7).

$$\frac{I_{p2}}{4e} = \left(\frac{D_1 A_1}{KTl_1}\frac{K_{NO}}{P_{N2}}P_{NOe}^2\right) \Big/ \left(1 + \frac{D_1 A_1 l_3}{D_3 A_3 l_1}\frac{1}{10^{(V_{p2}/0.05)} - K_3}\right) \quad (7)$$

Expression (7) represents the second pump current $I_{p2}$ corresponding to the partial pressure of NOx in the gas under measurement. Since, in expression (7), the second term in the denominator of the right-hand side is negligible with respect to the partial pressure $P_{NOe}$ of NOx in the gas under measurement, the second pump current $I_{p2}$ is proportional to the square of the partial pressure $P_{NOe}$ of NOx. Notably, the partial pressure $P_{NOe}$ of NOx corresponds to the NOx concentration. Accordingly, the second pump current $I_{p2}$ is proportional to the square of the concentration of NOx in the gas under measurement.

Another way of considering the invention is that the oxygen concentration in the second chamber is proportional to the partial pressure of oxygen that is dissociated from NO. From expression (6), the amount of oxygen is related to the square of the amount of the NO component in the gas. The amount of oxygen (that is included in $I_{p2}$ of FIG. 1) can thus be used to derive the concentration of NO using a non-linear expression. This also explains why the actually measured value of $I_{p2}$ is related to the square of Nox concentration when the Nox amount is very low, such as less than about 30 ppm.

(Second Embodiment)

A second embodiment of the present invention will next be described.

A method for measuring the concentration of NOx in a gas under measurement according to the second embodiment also measures the first pump current $I_{p1}$ and the second pump current $I_{p2}$ by use of the NOx concentration sensor 1 of FIG. 1.

Then, the NOx concentration obtained by the aforementioned expression (1) is taken as a provisional NOx concentration (hereinafter referred to as "NO'"). The offset component β is obtained from the first pump current $I_{p1}$ as described previously.

Next, the provisional NOx concentration NO' is substituted into expression (8), thereby obtaining the concentration of NOx in the gas under measurement.

$$NOx\ \text{concentration} = \frac{-d + \sqrt{d^2 + 4cNO'}}{2c} \quad (8)$$

$$= \frac{-d + \sqrt{d^2 + 4cG(I_{p2} - \beta)}}{2c}$$

where β: Offset component of second pump current $I_{p2}$
c, d: Constants (coefficients)

The constants c and d can be obtained from the relationship between the provisional NOx concentration NO' and the NOx concentration as measured by use of a standard gas as a gas under measurement.

The first embodiment utilises the phenomenon that the second pump current $I_{p2}$ is proportional to the square of the NOx concentration and directly obtains the NOx concentration from the second pump current $I_{p2}$ by use of expression (2) of second order.

By contrast, the second embodiment indirectly obtains the NOx concentration utilizing the phenomenon that the second pump current $I_{p2}$ is proportional to the square of the NOx concentration. Specifically, the provisional NOx concentration NO' is first obtained by use of the linear expression (1) representing the approximation of the second pump current $I_{p2}$ being proportional to the NOx concentration. The provisional NOx concentration NO' is then corrected by use of expression (8) of square root, thereby obtaining an accurate NOx concentration.

As in the case of the first embodiment, the second embodiment utilizes the phenomenon that the second pump current $I_{p2}$ is proportional to the square of the concentration of NOx in the gas under measurement, for measuring the NOx concentration in a measurement region in which the second pump current $I_{p2}$ has a low value, whereby the NOx concentration can be measured accurately even in a measurement region in which NOx concentration is low.

(Third Embodiment)

A third embodiment of the present invention will next be described.

A method for measuring the concentration of NOx in a gas under measurement according to the third embodiment also measures the first pump current $I_{p1}$ and the second pump current $I_{p2}$ by use of the NOx concentration sensor 1 of FIG. 1. The NOx concentration obtained by the aforementioned expression (1) is taken as the provisional NOx concentration NO'.

Next, the provisional NOx concentration NO' and the second pump current $I_{p2}$ are substituted into expression (9), thereby obtaining the concentration of NOx in the gas under measurement.

$$NOx\ \text{concentration} = NO' + f(I_{p2} - \beta)^2 + g(I_{p2} - \beta) \quad (9)$$

$$= G(I_{p2} - \beta) + f(I_{p2} - \beta)^2 + g(I_{p2} - \beta)$$

$$= (I_{p2} - \beta)(G + g) + f(I_{p2} - \beta)^2$$

where
β: Offset component of second pump current $I_{p2}$
G: Gain
f, g: Coefficients The constants f and g can be obtained in terms of coefficients of expression (10) of second order, which approximates the relationship between the deviation Δ(a difference obtained by subtracting the provisional NOx concentration NO' from the NOx concentration as measured by use of a standard gas as a gas under measurement) and the second pump current $I_{p2}$.

$$\Delta = f(I_{p2} - \beta)^2 + g(I_{p2} - \beta) \quad (10)$$

According to the third embodiment, the provisional NOx concentration NO' is first obtained by use of the linear expression (1) representing the approximation of the second pump current $I_{p2}$ being proportional to the NOx concentration. The deviation Δ (a difference obtained by subtracting the provisional NOx concentration NO' from the NOx concentration as measured by use of a standard gas as a gas under measurement) obtained by use of expression (10) of second order is added to the provisional NOx concentration NO' to thereby obtain an accurate NOx concentration.

As in the case of the first embodiment, the third embodiment utilizes the phenomenon that the second pump current $I_{p2}$ is proportional to the square of the concentration of NOx in the gas under measurement, for measuring the NOx concentration in a measurement region in which the second pump current $I_{p2}$ has a low value, whereby the NOx concentration can be measured accurately even in a measurement region in which NOx concentration is low.

Also, expressions (9) and (10) of the third embodiment do not involve computation for obtaining a square root. Accordingly, when a microcomputer is employed for calculating the NOx concentration, calculation speed can be increased. Therefore, in the case where the NOx concentration sensor 1 is mounted in a car in order to control the internal combustion engine of the car on the basis of the NOx concentration measured by the NOx sensor 1, speed in calculating the NOx concentration by an onboard ECU can be increased, thereby enabling highly accurate control of the internal combustion engine.

The present invention is not limited to the above-described embodiments, but may be modified as described below. Even in the case of such modification, actions and effects are obtained similar to those obtained by the above embodiments.

In the above embodiments, the NOx concentration is approximated by the expressions of second order which contain the second pump current $I_{p2}$. However, the NOx concentration may be approximated by, for example, an expression of third or higher order, an exponential function, or a logarithmic function. That is, the NOx concentration can be approximated by a nonlinear expression which contains the second pump current $I_{p2}$.

The present invention may be applied to measurement of the concentrations of other gases (for example, $COx$, $H_2O$, and HC) by selecting respectively appropriate voltages to be applied to the second oxygen ion pump cell 8 so as to selectively decompose the gases. By storing these respective conditions in the memory of a single concentration sensor, the concentration sensor can measure the concentrations of component gases, such as $O_2$, $Ox$, $CO_2$, and $H_2O$, in a multicomponent gas.

By way of example, with $H_2O$-gas measurement the following equilibrium exists:

$$2H_2O \rightleftharpoons 2H_2 + O_2$$

which leads to the partial pressure relationship:

$$P_{O2} = K_{P\ H2O} * P_{H2O}^2 / P_{H2}^2$$

This is analogous to expression (6) above and thus also shows that the $H_2O$ concentration can be obtained using a non-linear relationship from the oxygen concentration.

While the invention has been described in detail and with reference to specific embodiments thereof, it will be apparent to one skilled in the art that various changes and modifications can be made therein without departing from the spirit and scope thereof.

What is claimed is:

1. A method for measuring the concentration of a component of a gas under measurement by use of a sensor comprising: a first chamber equipped with a first oxygen ion pump cell, which comprises a solid electrolyte layer and a pair of electrodes; a second chamber equipped with a second oxygen ion pump cell, which comprises a solid electrolyte layer and a pair of electrodes; a first diffusion passage for establishing communication between the first chamber and the gas under measurement; and a second diffusion passage for establishing communication between the first chamber and the second chamber;

said method comprising the steps of:
applying a pump voltage to the first oxygen ion pump cell so as to reduce the concentration of oxygen in the gas under measurement to be introduced into the second chamber;
introducing into the second chamber through the second diffusion passage the gas under measurement which has undergone reduction of oxygen concentration within the first chamber, and applying a pump voltage to the second oxygen ion pump cell;
measuring a first pump current flowing through the first oxygen ion pump cell;
measuring a second pump current flowing through the second oxygen ion pump cell; and
obtaining from the second pump current the concentration of said component in the gas under measurement introduced into the first chamber by use of a non-linear expression which expresses an approximated relationship between the second pump current and the concentration of said component in the gas under measurement, wherein the concentration of the component of the gas under measurement is 100 ppm or less.

2. A method according to claim 1, wherein said nonlinear expression is:

$$\text{concentration} = \frac{b + \sqrt{b^2 + 4a(I_{p2} - \beta)}}{2a}$$

where: $I_{p2}$ is said second pump current; and a is coefficient; and b and β are constants.

3. A method according to claim 1, which comprises obtaining a provisional component concentration from the second pump current by use of a linear expression which approximates the concentration in terms of the second pump current; and correcting the obtained provisional concentration by use of an expression of higher order to thereby obtain the concentration of the component in the gas under measurement introduced into the first chamber.

4. A method according to claim 3, wherein said expression of higher order is:

$$\text{concentration} = \frac{-d + \sqrt{d^2 + 4cX}}{2c}$$

where: X is the provisional concentration; and c and d are a coefficient and a constant, respectively.

5. A method according to claim 4, wherein said linear expression is:

$$X = G(I_{p2} - \beta)$$

where: X is said provisional concentration; $I_{p2}$ is said second pump current; and G and β are a coefficient and a constant, respectively.

6. A method according to claim 1, which comprises obtaining a provisional component concentration from the second pump current by use of a linear expression which approximates the concentration in terms of the second pump current, and adding a deviation of the provisional concentration from an actual concentration as approximated by an expression of higher order to the provisional concentration to thereby obtain the concentration of the component in the gas under measurement introduced into the first chamber.

7. A method according to claim 6, wherein said concentration is obtained by:

concentration=$X+\Delta$ where X is the provisional concentration, $\Delta$ is the deviation, and said expression of higher order is:

$\Delta=f(I_{p2}-\beta)^2+g(I_{p2}-\beta)$ where: $I_{p2}$ is said second pump current; and f and g are coefficients; and $\beta$ is a constant.

8. A method according to claim 7, wherein said $X=G(I_{p2}-\beta)$ where: X is said provisional concentration; $I_{p2}$ is said second pump current; and G and $\beta$ are a coefficient and a constant, respectively.

9. A method according to claim 1, said method further comprising the step of obtaining the concentration of oxygen in the gas under measurement introduced into the first chamber from the first pump current by use of a linear expression which expresses an approximated relationship between the first pump current and the concentration of oxygen in the gas under measurement.

10. A method for measuring the concentration of a component in a gas under measurement according to claim 1, wherein said nonlinear expression includes one or more coefficients, and at least one coefficient of the nonlinear expression is obtained from the first pump current and/or the second pump current.

11. A method according to claim 10, wherein at least one of said coefficients is predetermined in a calibration step by the use of one or more gases having a component of known concentration.

12. A method according to claim 1, wherein the component of the gas under measurement is selected from the group consisting of NOx, $CO_2$, $H_2O$ and HC.

13. A method according to claim 1, wherein the concentration of the component of the gas under measurement is 30 ppm or less.

14. A method according to claim 13, wherein nitrogen monoxide in said first and second chambers undergoes decomposition.

15. A method according to claim 1, wherein said component of the gas under measurement is NOx.

16. An apparatus for measuring the concentration of a component of a gas under measurement, said apparatus comprising: a first chamber equipped with a first oxygen ion pump cell, which comprises a solid electrolyte layer and a pair of electrodes; a second chamber equipped with a second oxygen ion pump cell, which comprises a solid electrolyte layer and a pair of electrodes; a first diffusion passage for establishing communication between the first chamber and the gas under measurement; a second diffusion passage for establishing communication between the first chamber and the second chamber; a circuit for applying a pump voltage to the first oxygen ion pump cell so as to reduce the concentration of oxygen in the gas under measurement to be introduced into the second chamber; a circuit for applying a pump voltage to the second oxygen ion pump cell; means for measuring a first pump current flowing through the first oxygen ion pump cell; means for measuring a second pump current flowing through the second oxygen ion pump cell; and means for obtaining from the second pump current, the concentration of said component in the gas under measurement introduced into the first chamber by use of a non-linear expression which expresses an approximated relationship between the second pump current and the concentration of said component in the gas under measurement, wherein the concentration of the component of the gas under measurement is 100 ppm or less.

* * * * *